United States Patent
Balachandran

(10) Patent No.: US 7,329,791 B2
(45) Date of Patent: Feb. 12, 2008

(54) HYDROGEN TRANSPORT MEMBRANES FOR DEHYDROGENATION REACTIONS

(75) Inventor: Uthamalingam Balachandran, Hinsdale, IL (US)

(73) Assignee: UChicago Argonne, LLC, Chicago, IL (US)

( * ) Notice: Subject to any disclaimer, the term of this patent is extended or adjusted under 35 U.S.C. 154(b) by 673 days.

(21) Appl. No.: 10/814,210

(22) Filed: Mar. 31, 2004

(65) Prior Publication Data

US 2005/0222479 A1 Oct. 6, 2005

(51) Int. Cl.
*C07C 5/333* (2006.01)
*C07C 5/327* (2006.01)
*C07C 7/144* (2006.01)
*B01D 53/22* (2006.01)

(52) U.S. Cl. .............. 585/660; 585/654; 585/661; 585/818; 95/56

(58) Field of Classification Search .......... 585/654, 585/660, 818, 661; 95/56
See application file for complete search history.

(56) References Cited

U.S. PATENT DOCUMENTS

| | | | |
|---|---|---|---|
| 4,313,013 A * | 1/1982 | Harris | ............ 585/818 |
| 5,030,661 A | 7/1991 | Lywood | |
| 5,447,559 A | 9/1995 | Rao et al. | |
| 5,645,626 A | 7/1997 | Edlund et al. | |
| 5,725,633 A | 3/1998 | Ozcayir et al. | |
| 5,980,989 A * | 11/1999 | Takahashi et al. | ............ 427/294 |
| 6,066,592 A | 5/2000 | Kawae et al. | |
| 6,569,226 B1 * | 5/2003 | Dorris et al. | ............ 95/56 |

* cited by examiner

*Primary Examiner*—Glenn A. Caldarola
*Assistant Examiner*—In Suk Bullock
(74) *Attorney, Agent, or Firm*—Olson & Cepuritis, Ltd.; Harry M. Levy

(57) ABSTRACT

A method of converting $C_2$ and/or higher alkanes to olefins by contacting a feedstock containing $C_2$ and/or higher alkanes with a first surface of a metal composite membrane of a sintered homogenous mixture of an Al oxide or stabilized or partially stabilized Zr oxide ceramic powder and a metal powder of one or more of Pd, Nb, V, Zr, Ta and/or alloys or mixtures thereof. The alkanes dehydrogenate to olefins by contact with the first surface with substantially only atomic hydrogen from the dehydrogenation of the alkanes passing through the metal composite membrane. Apparatus for effecting the conversion and separation is also disclosed.

29 Claims, 1 Drawing Sheet

HYDROGEN TRANSPORT MEMBRANES FOR DEHYDROGENATION REACTIONS

CONTRACTUAL ORIGIN OF THE INVENTION

The United States Government has rights in this invention pursuant to Contract No. W-31-109-ENG-38 between the U.S. Department of Energy (DOE) and The University of Chicago representing Argonne National Laboratory.

BACKGROUND OF THE INVENTION

Current olefin (ethylene, propylene, and 1,3-butadiene) are made by cracking hydrocarbon feeds ranging from LPG to light naphtha in very large thermal steam crackers. In addition, the conversion yield and selectivity for both propylene and ethylene are poor using the current steam cracking procedure in addition to the following problems with large cracking plants.

There are three drawbacks to large crackers. First, to be competitive, they need to produce at least a 1 billion pounds/year of ethylene. The cost of building units this large is about one dollar for each lb/year of ethylene produced or about 1 billion dollars/unit. Second, while there is some flexibility in the product output based on feed and operating conditions, this is rather limited and these units invariably produce one or more low value products(s) that the operators would rather not make. Third, they operate at high temperatures (800 to 1200 degrees F.) and are very energy intensive. Moreover, the thermal cracking reaction is highly endothermic (substantial energy input is required); the equilibrium conversion is thermodynamically limited and selectivity declines at higher temperatures; carbon oxide formation occurs; side reactions occur (undesired product formation) requiring extensive product purification. While a number of schemes have been proposed to couple olefin formation with further down stream products to improve efficiencies, they have not found wide-spread commercial application. Olefins (alkenes), such as ethylene ($C_2H_4$) and propylene ($C_3H_6$), are among the primary sources of starting materials for the chemical industry.

About 60 billion pounds of ethylene is produced annually in the USA. It is the starting material for polyethylene, ethylene copolymers, ethylene glycol, ethylene oxide, (surfactants and detergents), etc. There is a commercial need for process technology that provides an economical alternative for smaller units which operate with improved product output flexibility.

SUMMARY OF THE INVENTION

This invention relates to a method of and apparatus for dehydrogenating hydrocarbons thereby producing high value-added chemicals and feed stocks. More specifically this invention relates to a method and apparatus which utilizes hydrogen transport membranes to dehydrogenate hydrocarbons to form olefins.

Accordingly, a principle object of the present invention is to provide a method and apparatus for the non-galvanic production of olefins from alkanes.

Yet another object of the present invention is to provide a method and apparatus for converting alkanes to olefins with a high yield and excellent selectivity, in excess reached by steam cracking.

A further object of the present invention is to provide a method of converting $C_2$ and/or higher alkanes to olefins, comprising contacting a feedstock containing $C_2$ and/or higher alkanes with a first surface of a metal composite membrane of a sintered homogenous mixture of a metal oxide ceramic powder and a metal powder of one or more of Pd, Nb, V, Zr, Ta and/or alloys or mixtures thereof, wherein the $C_2$ and/or higher alkanes dehydrogenate to olefins by contact with the first surface with hydrogen from the dehydrogenation of the alkanes passing through the metal composite membrane to a second surface, and separating the formed olefins from the first surface of the membrane while separating the hydrogen from the second surface.

Yet another object of the present invention is to provide a method of converting $C_2$ and/or higher alkanes to olefins, comprising contacting a feedstock containing $C_2$ and/or higher alkanes with a first surface of a metal composite membrane of a sintered homogenous mixture of an Al oxide or a stabilized or partially stabilized Zr oxide ceramic powder and a metal powder of one or more of Pd, Nb, V, Zr, Ta and/or alloys or mixtures thereof, wherein the $C_2$ and/or higher alkanes dehydrogenate to olefins by contact with the first surface with substantially only atomic hydrogen from the dehydrogenation of the alkanes passing through the metal composite membrane to a second surface, and separating the formed olefins from the first surface of the membrane while separating the hydrogen from the second surface.

A still further object of the present invention is to provide an apparatus for converting $C_2$ and/or higher alkanes to olefins, comprising a supply of feedstock containing $C_2$ and/or higher alkanes, a metal composite membrane of a sintered homogenous mixture of a metal oxide ceramic powder and a metal powder of one or more of Pd, Nb, V, Zr, Ta and/or alloys or mixtures thereof, mechanism for contacting the feedstock with one side of the membrane wherein the $C_2$ and/or higher alkanes dehydrogenate to olefins by contact with the membrane with atomic hydrogen from the dehydrogenation of the alkanes passing through the membrane to another side thereof, and mechanism for separating the formed olefins from one side of the membrane while separating atomic hydrogen from the other side.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

DESCRIPTION OF THE PREFERRED EMBODIMENT

Figure 1:
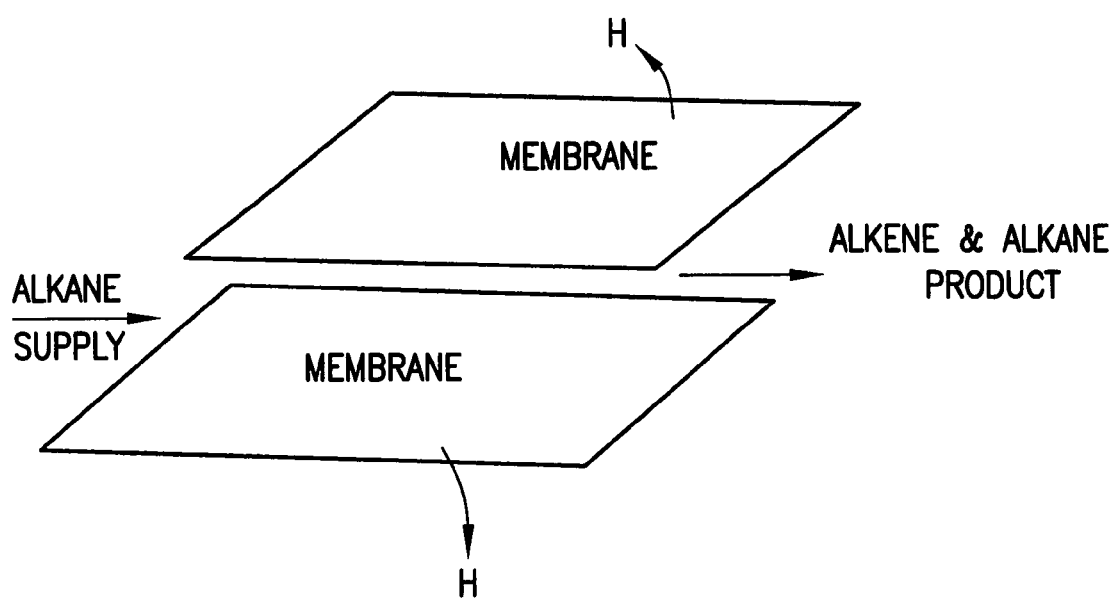
FIG. 1 is a schematic illustration of the use of a dual phase membrane for converting alkanes to alkenes.

This invention relates to membranes disclosed in U.S. Pat. No. 6,569,226 issued May 27, 2003, the entire disclosure of which is incorporated by reference. The membranes of the present invention may be in sheet form or tubular form or honeycomb form, the latter being illustrated in U.S. Pat. No.

5,356,728 issued Oct. 18, 1994, the entire disclosure of which is incorporated herein by reference. Membranes of the type disclosed in the '226 patent separate hydrogen from a feedstock containing hydrogen. However, it is has been discovered that when feedstocks contain alkanes, use of the membranes disclosed in the '226 patent remove hydrogen from the alkanes converting same to alkenes or olefins with very high activity and very high yield. While the membranes disclosed in the '226 patent are operable for the present invention, it has been found that certain of the membranes which pass or are permeable to atomic hydrogen rather than protons and which do not pass electrons are preferable for the present invention. More particularly, as disclosed in the '226 patent, there is a homogeneous mixture of a metal powder and a oxide ceramic powder. Metal powders may be selected from palladium, niobium, tantalum, zirconium, vanadium, alloys thereof and various mixtures or combinations thereof. The oxygen containing ceramic may be preferably selected from alumina, barium titanate, strontium titanate, zirconia stabilized or partially stabilized with yttria or calcia and various combinations thereof. Of the previously recited metal components, palladium and/or palladium alloys containing silver or copper are preferred. Moreover, palladium silver alloys in which silver is present in the range of from about 20-25% by weight is preferred and a palladium silver alloy wherein silver is present at about 23% by weight is most preferred. With respect to the palladium copper alloys, preferred alloys are where copper is present in the range of from about 30-55% by weight and most preferred is the palladium copper alloy wherein copper is present at about 40% by weight. Of the preferred oxide ceramics, alumina and zirconia stabilized or partially stabilized with yttria or calcia are preferred because they are not electron conductors, while the metallic component transports atomic hydrogen rather than protons.

As indicated in the '226 patent, the metal powder component of the homogeneous mixture which is sintered and forms a membrane is preferably present in an amount in the range of from about 20 to about 60 volume percent of the membrane, that is the ceramic portion is preferably present in the range of from about 40 to about 80 percent by volume of the membrane material. Moreover, the sintered mixture is preferably homogeneous and has substantially no interconnected porosity. Although the '226 patent speaks of no interconnected porosity, it is recognized that "no" is an absolute term and those of ordinary skill in the art would not understand that "no interconnected porosity" means substantially none. Membranes of the present invention may have a thickness in the range of from about 0.01 mm to about 5 mm and the density is generally greater than 95% of theoretical. As taught in the '226 patent, 97% of theoretical density is also obtainable and generally the denser the better.

In a test with alkane feedstocks, membranes of the present invention particularly yittria stabilized zirconia membranes using a palladium phase have been greater than 90% selective for propane and converting up to about 76% of the propane to propylene. Although the examples described herein relate to ethane and propane, it should be recognized that higher alkanes may also be converted as may mixtures of alkanes. The selectivity of the present membrane for converting alkanes to alkenes is significant as is the efficiency in converting alkanes to alkenes or olefins.

As is well understood by one of ordinary skill in the chemical arts, it is preferable to drive the reaction and therefore, the hydrogen should be removed from the side of the membrane from which it is produced and this may be accomplished by using a sweep gas, a vacuum or any other means commonly used in the chemical engineering arts. Moreover, the reaction may be driven by using a pressure gradient across the membrane or by any other means well known in the chemical arts.

As indicated above, the physical form of the membrane may be almost any engineering shape. For instance it may be flat sheets as used in many heat exchangers or it may be a combination of sheets or corrugated and honeycomb material as disclosed in the incorporated '728 patent or tubular material as disclosed in the '226 patent. The physical shape of the membranes is almost irrelevant to the invention, it being a matter of design choice in the particular construction used to convert alkanes to alkenes.

Also included in the invention is an apparatus for converting alkanes to alkenes as seen in FIG. 1 in which a supply of feedstock containing the feed material is in fluid communication with the metal composite membrane as previously disclosed along with mechanism for contacting the feedstock with one side of the membrane and mechanism for separating the atomic hydrogen from the other side of the membranes. The formed olefins which are on the same side of the membrane as the feedstock can be separated by means and mechanism apparatus well known in the chemical arts.

The membranes of the present invention may operate in a wide variety of temperatures and pressures (see the '226 patent) but for converting propane to propylene, a temperature of from about 835° C. to about 850° C. may be conveniently used. The membranes are stable well past 900° C. and may be used, with the appropriate engineering design up to about 1000 psi. The conversion, most importantly, occurs non-galvanically and represents a significant improvement not only in selectivity and efficiency but also in the cost of designing and maintaining a conversion plant as compared to steam reforming and other currently used cracking methods.

While there has been disclosed what is considered to be the preferred embodiment of the present invention, it is understood that various changes in the details may be made without departing from the spirit, or sacrificing any of the advantages of the present invention.

The embodiments of the invention in which an exclusive property or privilege is claimed are defined as follows:

1. A method of converting $C_2$ and/or higher alkanes to olefins, comprising contacting a feedstock containing $C_2$ and/or higher alkanes with a first surface of a metal composite membrane of a sintered homogenous mixture of a metal oxide ceramic powder including stabilized or partially stabilized $ZrO_2$ and a metal powder of one or more of Pd, Nb, V, Zr, Ta and/or alloys or mixtures thereof, wherein the $C_2$ and/or higher alkanes dehydrogenate to olefins by contact with the first surface with hydrogen from the dehydrogenation of the alkanes passing through the metal composite membrane to a second surface, and separating the formed olefins from the first surface of the membrane while separating the hydrogen from the second surface.

2. The method of claim 1, wherein the feedstock contains ethane.

3. The method of claim 1, wherein the feedstock contains propane.

4. The method of claim 1, wherein the membrane contains Pd.

5. The method of claim 1, wherein the membrane contains a Pd—Ag alloy.

6. The method of claim 1, wherein the membrane contains a Pd—Ag alloy with Ag present in the range of from about 20 to about 25% by weight.

7. The method of claim 1, wherein the membrane contains a Pd—Ag alloy with Ag present at about 23% by weight.

8. The method of claim 1, wherein the membrane contains a Pd—Cu alloy.

9. The method of claim 1, wherein the membrane contains a Pd—Cu alloy with Cu present in the range of from about 30 to about 55% by weight.

10. The method of claim 1, wherein the membrane contains a Pd—Cu alloy with Cu present at about 40% by weight.

11. The method of claim 1, wherein the metal oxide ceramic powder further contains one or more of $Al_2O_3$, $BaTiO_3$, and $SrTiO_3$.

12. The method of claim 1, wherein the metal oxide ceramic powder contains yttria stabilized $ZrO_2$.

13. The method of claim 1, wherein the metal oxide ceramic powder contains calcia stabilized $ZrO_2$.

14. The method of claim 1, wherein the membrane is not less than about 95% of theoretical density.

15. The method of claim 1, wherein the membrane has a thickness in the range of from about 0.01 millimeters to about 5 millimeters.

16. The method of claim 1, wherein the membrane is in the form of a sheet or a tube or a honeycomb.

17. The method of claim 1, wherein the metal powder is present in the membrane in the range of from about 20 to about 60% by volume.

18. The method of claim 1, wherein the membrane is permeable to atomic hydrogen and has substantially no interconnected porosity.

19. A method of converting $C_2$ and/or higher alkanes to olefins, comprising contacting a feedstock containing $C_2$ and/or higher alkanes with a first surface of a metal composite membrane of a sintered homogenous mixture or stabilized or partially stabilized Zr oxide ceramic powder with or without Al oxide and a metal powder of one or more of Pd, Nb, V, Zr, Ta and/or alloys or mixtures thereof, wherein the $C_2$ and/or higher alkanes dehydrogenate to olefins by contact with the first surface with substantially only atomic hydrogen from the dehydrogenation of the alkanes passing through the metal composite membrane to a second surface, and separating the formed olefins from the first surface of the membrane while separating the hydrogen from the second surface.

20. The method of claim 19, wherein the feedstock contains ethane or propane.

21. The method of claim 19, wherein the membrane contains Pd.

22. The method of claim 19, wherein the membrane contains a Pd—Ag alloy.

23. The method of claim 19, wherein the membrane contains a Pd—Ag alloy with Ag present in the range of from about 20 to about 25% by weight.

24. The method of claim 19, wherein the membrane contains a Pd—Cu alloy.

25. The method of claim 19, wherein the membrane contains a Pd—Cu alloy with Cu present in the range of from about 30 to about 55% by weight.

26. The method of claim 19, wherein the stabilized or partially stabilized Zr oxide ceramic powder contains calcia or yttria stabilized $ZrO_2$.

27. The method of claim 19, wherein the stabilized or partially stabilized Zr oxide powder is yttria stabilized $ZrO_2$.

28. The method of claim 19, wherein the membrane is not less than about 95% of theoretical density.

29. The method of claim 19, wherein the membrane has a thickness in the range of from about 0.01 millimeters to about 5 millimeters and is permeable to atomic hydrogen with substantially no interconnected porosity.

* * * * *